(12) United States Patent
Bazou et al.

(10) Patent No.: US 9,719,065 B2
(45) Date of Patent: Aug. 1, 2017

(54) METHOD OF FORMING A MULTILAYER AGGREGATE OF OBJECTS

(71) Applicant: CENTRE NATIONAL DE LA RECHERCHE SCIENTIFIQUE, Paris (FR)

(72) Inventors: Despina Bazou, Dublin (IE); Mauricio Hoyos, Creteil (FR); Luz Angelica Castro Camacho, Paris (FR)

(73) Assignee: CENTRE NATIONALE DE RECHERCHE SCIENTIFIQUE, Paris (FR)

( * ) Notice: Subject to any disclaimer, the term of this patent is extended or adjusted under 35 U.S.C. 154(b) by 380 days.

(21) Appl. No.: 14/376,947

(22) PCT Filed: Feb. 5, 2013

(86) PCT No.: PCT/IB2013/050958
§ 371 (c)(1),
(2) Date: Aug. 6, 2014

(87) PCT Pub. No.: WO2013/118053
PCT Pub. Date: Aug. 15, 2013

(65) Prior Publication Data
US 2015/0037863 A1    Feb. 5, 2015

(30) Foreign Application Priority Data
Feb. 6, 2012   (EP) .................................... 12154125

(51) Int. Cl.
*G01N 1/40* (2006.01)
*C12N 5/00* (2006.01)
(Continued)

(52) U.S. Cl.
CPC ......... *C12N 5/0062* (2013.01); *C12N 5/0693* (2013.01); *C12N 2513/00* (2013.01);
(Continued)

(58) Field of Classification Search
CPC ............ C12N 2521/10; C12N 2513/00; C12N 5/0062; C12N 5/0693; G01H 17/00;
(Continued)

(56) References Cited

U.S. PATENT DOCUMENTS 6,216,538 B1 * 4/2001 Yasuda ................ B01D 21/283
210/748.05
2008/0067128 A1   3/2008 Hoyos et al.
(Continued)

FOREIGN PATENT DOCUMENTS

WO   WO 2010/135044 A1   11/2010
WO   WO 2013128224 A1 *  9/2013 ........... C12N 5/0062

OTHER PUBLICATIONS

Callens et al., "Particle Sorting in a Mini Step-Split-Flow Thin Channel: Influence of Hydrodynamic Shear on Transversal Migration," *Analytical Chemistry*, 2008, vol. 80, No. 13, pp. 4866-4875.
(Continued)

*Primary Examiner* — Laura Martin
*Assistant Examiner* — Rose M Miller
(74) *Attorney, Agent, or Firm* — Oliff PLC

(57) ABSTRACT

A method of forming a multilayer aggregate of objects in a channel including a liquid, the method including: a) providing objects at first and second superposed regions of the channel, b) obtaining first and second aggregates of objects, optionally by applying transverse acoustic waves, preferably stationary waves, within each region to objects, and c) bringing the first and second aggregates into contact to form the multilayer aggregate of objects by submitting the first and second aggregates to: gravity in absence of acoustic waves, or to acoustic waves, optionally stationary waves, inducing displacement of the first and second aggregates toward each other.

32 Claims, 6 Drawing Sheets

(51) Int. Cl.
*C12N 5/09* (2010.01)
*G01N 15/14* (2006.01)

(52) U.S. Cl.
CPC .. *C12N 2521/10* (2013.01); *G01N 2001/4094* (2013.01); *G01N 2015/142* (2013.01)

(58) Field of Classification Search
CPC ............... B01D 21/28; Y10T 137/0324; Y10T 137/206; G01N 15/1459; G01N 15/06; G01N 15/14; G01N 1/40; G01N 2001/4094; G01N 2001/4077; G01N 2015/1413; G01N 2015/1459; G01N 2015/142; G01N 2015/1081; G01N 2015/1087; G01N 2015/1093
USPC .............................................. 73/570.5, 61.75
See application file for complete search history.

(56) References Cited

U.S. PATENT DOCUMENTS

| | | | | |
|---|---|---|---|---|
| 2008/0220515 | A1* | 9/2008 | McCall | C12M 21/02 435/292.1 |
| 2009/0169428 | A1* | 7/2009 | Gillespie | G01N 15/1484 422/68.1 |
| 2011/0278218 | A1* | 11/2011 | Dionne | B01D 17/04 210/523 |
| 2013/0327130 | A1* | 12/2013 | Hoyos | G01N 15/06 73/61.75 |
| 2014/0011240 | A1* | 1/2014 | Lipkens | B01D 21/28 435/71.1 |
| 2016/0208213 | A1* | 7/2016 | Doyle | C12N 5/0062 |

OTHER PUBLICATIONS

Ratier et al., "Acoustic Programming in Step-Split-Flow Lateral-Transport Thin Fractionation," *Analytical Chemistry,* 2010, vol. 82, No. 4, pp. 1318-1325.

Kuznetsova et al., "Multiple Three-Dimensional Mammalian Cell Aggregates Formed Away from Solid Substrata in Ultrasound Standing Waves," Biotechnology Progress, 2009, vol. 25, No. 3, pp. 834-841.

Bazou et al., "Long-Term Viability and Proliferation of Alginate-Encapsulated 3-D HepG2 Aggregates Formed in an Ultrasound Trap," *Toxicology in Vitro,* 2008, vol. 22, No. 5, pp. 1321-1331.

Bazou et al., "Controlled Cell Aggregation in a Pulsed Acoustic Field," *Ultrasonics,* 2012, vol. 52, No. 7, pp. 842-850.

Williams et al., "Characterization of Nonspecific Crossover in Split-Flow Thin Channel Fractionation," *Analytical Chemistry,* 2008 ,vol. 80, No. 18, pp. 7105-7115.

International Search Report issued in International Application No. PCT/IB2013/050958 mailed Apr. 25, 2013.

Written Opinion of the International Searching Authority issued in International Application No. PCT/IB2013/050958 mailed Apr. 25, 2013.

European Search Report issued in European Application No. 12154125.4 issued Jul. 26, 2012.

* cited by examiner

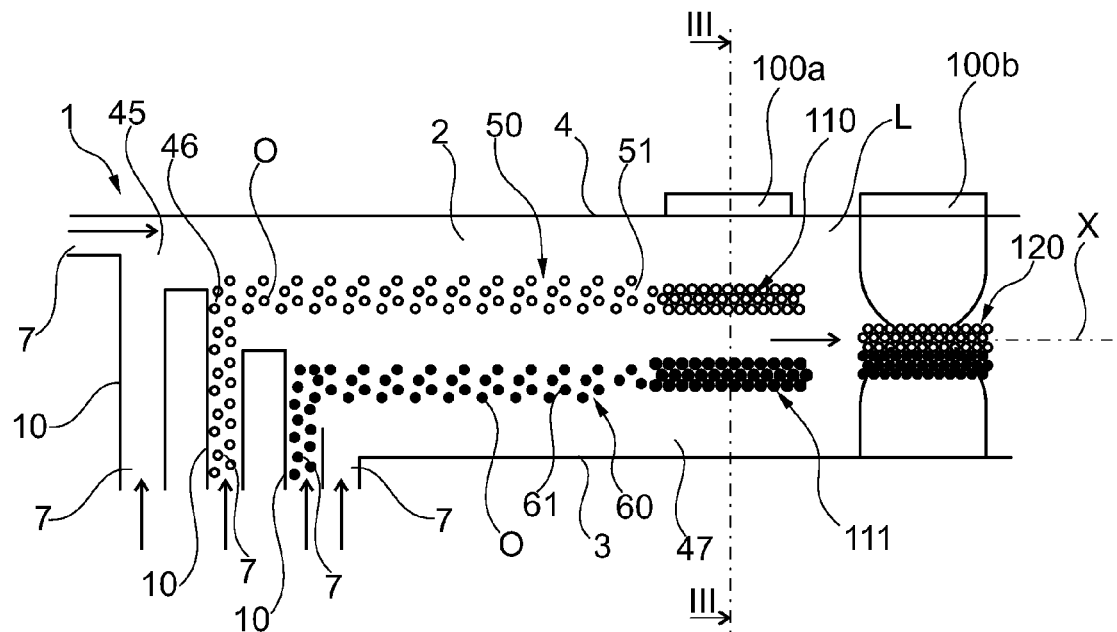
Fig. 1
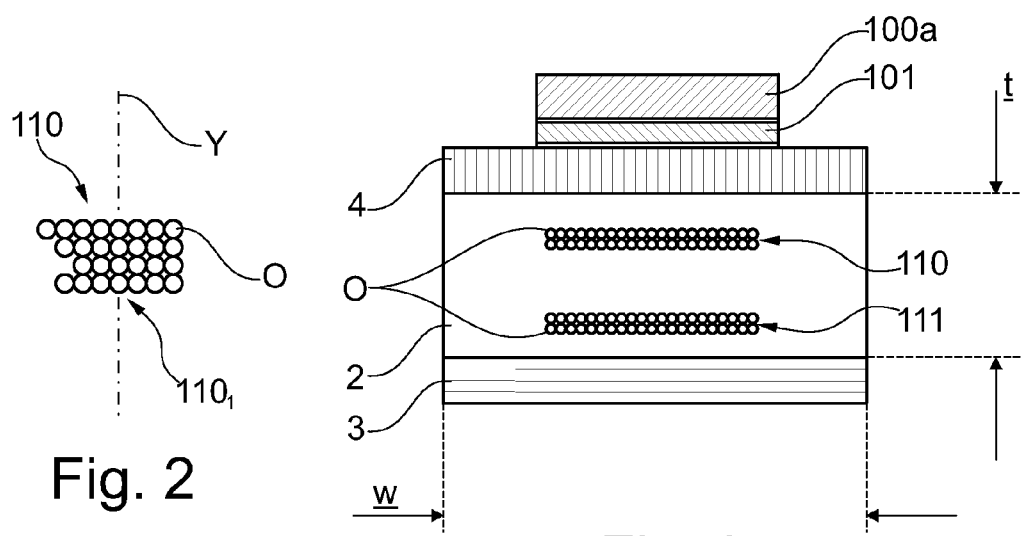
Fig. 2
Fig. 3

METHOD OF FORMING A MULTILAYER AGGREGATE OF OBJECTS

The present invention relates to methods of forming a multilayer aggregate of objects in a channel comprising a liquid.

BACKGROUND

The field of tissue engineering presents an exciting avenue for regenerative therapies by combining biomaterials with living cells. The combination of novel biomaterials (scaffolds) with living cells has yielded some clinical success in the reconstruction of a wide range of functional tissues such as, for example, bone, arteries, and bladders. However, due to inflammatory responses and pathological fibrotic states arising following scaffold biodegradation, a novel tissue engineering methodology, called "cell sheet engineering" that constructs 3-D functional tissues by layering two-dimensional cell sheets without the use of any biodegradable extracellular matrix alternatives, has emerged.

Still, the principal shortcoming of cell sheets is their poor mechanical properties when related to functional applications. Cell sheets contract extensively when removed from culture surfaces resulting in reduced graft sizes. In clinical settings it will be ideal to control the specific graft size and shape for specific applications. In addition, the fragility of cell sheets makes handling difficult. Methods to resolve these problems still remain a significant obstacle in the effective reconstruction of mechanically robust and manipulable 3-D tissues even when scaffold-based technologies are avoided.

As regenerative medicine therapies become more advanced there is an increasing need to develop strategies for the scale up of cell and tissue culture to meet predicted demands. In response, there is interest in the use of automated cell and tissue culture systems, the success of which, being dependent on monitoring and control strategies. There are various culture techniques to generate in vitro 2- and 3-D aggregates in suspension, such as 2-D cell seeding on flat and rigid plastic/glass surfaces, pellet, spheroid and hanging drop culture, scaffolding, liquid overlay, spinner flask and the gyratory rotation technique [4]. However, these methods may be limited by either long cultivation time, formation of unequally-sized aggregates or difficult mechanical accessibility. Consequently they may not be suitable for a standardised, rapid and large scale production of 2-/3-D aggregates in a format needed for high-throughput assays Manipulating micron and submicron sized particles can be accomplished using an acoustic force, $Fa=V\langle e \rangle k \tilde{A} \sin(2ky)$, generated by an acoustic stationary field acting in a thin chamber. V is the volume of the particle, $\langle e \rangle$ is the average acoustic energy, $k=2\pi/\lambda$ is the wave number and $\tilde{A}$ is the acoustic contrast factor that depends on the acoustic properties of particles and suspending fluid.

This chamber may be called an "acoustic resonator". This resonator may comprise an emitting wall and a reflective wall. The standing wave may occur when the thickness of the chamber w and the acoustic wavelength $\lambda$ are related as shown in the following equation: $w=n\lambda/2$ where n is the number of nodes created in the thickness of the chamber. Particles subjected to this force field acoustic variable in thickness, may be pushed to the nodes or antinodes of the standing waves, depending on the acoustic contrast factor $\tilde{A}$, which is a function of the acoustic impedances defined as the product $\rho_i c_i$, where $\rho_i$ and $c_i$ are the densities and the sound velocities of the fluid or of the suspended particles.

It would also be interesting to develop techniques of tissue engineering for astronaut needs. In weightlessness conditions in space, cell culture is a challenge because cells in culture medium are wandering inside the reactor and are not naturally directed toward a scaffold or a matrix where the aggregate and further tissue has to growth. Forming an aggregate in weightlessness may further take days.

A need exists for a method allowing rapid formation of 2- and 3-D cell aggregates that would be advantageous over the aforementioned conventional methods of cell culturing.

A need exists to obtain a method allowing the formation of multilayer structures consisting of biological objects such as cells.

Another need exists to obtain a method to generate tissue-mimetic constructs.

Another need exists to obtain improved techniques of tissue engineering.

The present invention aims to meet some or all of the aforementioned needs.

SUMMARY

According to a first aspect, the present invention provides a method of forming a multilayer aggregate of objects in a channel comprising a liquid, said method comprising:
 a) providing objects at first and second superposed regions of the channel,
 b) obtaining first and second aggregates of objects, and
 c) bringing said first and second aggregates into contact to form said multilayer aggregate of objects by submitting said first and second aggregates to:
  gravity in absence of acoustic waves, or to
  acoustic waves, optionally stationary waves, inducing displacement of said first and second aggregates toward each other.

By "aggregate of objects", it is meant a layer of objects satisfying all of the following features:
 at least two objects comprised in said layer, in particular at least 10%, better 25%, preferably 50% of the objects comprised in said layer, are in contact, and
 said layer presents, on at least a portion of its length, a succession of objects when displacing along at least one of its transverse dimensions.

The obtained aggregates may be 2D or 3D aggregates.

The obtained aggregates may extend in a plane and comprise, in particular consist in, juxtaposed rows of objects. In this case, the aggregates are referred to as 2D-aggregates.

In another embodiment, the obtained aggregates comprise a stacking of 2D-aggregates. Such an embodiment is an example of a 3D-aggregate.

An aggregate is different from a line of objects which only extend along an axis. In other words, a line of objects comprises only one object in width, only one object in thickness and a succession of objects along its length.

The present invention may advantageously allow collecting aggregates continuously without damage.

The present invention may advantageously allow the formation of multilayer aggregates of objects of the same or different species.

The present invention may advantageously enable controlled and programmed generation of cell aggregates (2- and/or 3-D) of identical dimensions.

The present invention may advantageously allow the simultaneous formation of 2-D cell sheets (homotypic and/ or heterotypic, i.e. same or different cell types) that will be positioned in a stratified manner in a minimally invasive way e.g. in order to generate tissue-mimetic constructs.

The present invention may advantageously allow manipulation and control of the aggregates and the avoidance of contact between the objects and the walls of the channel which may modify their properties.

The present invention further advantageously allows the quick obtaining of aggregates of objects, in particular 3-D cell aggregates.

The present invention advantageously allows the obtaining a multilayer aggregate using a device that can be manufactured relatively easily and which can be used in sterile conditions. The device used in the method according to the invention may comprise a standard ultrasound equipment.

Layers of objects at first and second superposed regions of the channel may be provided at step a), said layers optionally being obtained by a hydrodynamic focusing.

The objects present in the first region, at step a), may have a different size and/or nature from objects present, at step a), in the second region.

The first and second aggregates of objects may be obtained at step b) by application of transverse acoustic waves, optionally stationary waves, within each region.

In a variant, the first and second aggregates of objects may be obtained at step b) by a hydrodynamic focusing. In this case, the objects forming an aggregate may advantageously present surface interactions, e.g. electrostatic interactions, allowing them to move closer to one another.

According to one embodiment, the acoustic field is, in step c), terminated and the aggregates of objects are brought into contact due to gravity thus allowing said aggregates to be positioned on top of each other, e.g. leading to organized stratified tissue-mimetic constructs.

Such an embodiment may advantageously permit creation of cells arranged as cell sheets in suspension and thereby avoid contraction of the cell sheets. Such an embodiment is also minimally invasive and may facilitate handling.

According to some embodiments, step c) comprises submitting the aggregates to acoustic waves having:
 a different number of, optionally less, acoustic nodes than the acoustic waves applied at step b), and/or
 at least one acoustic node, respectively antinode, having a transverse position which is different from the transverse position(s) of the acoustic node(s), respectively antinode(s), of the acoustic waves applied at step b), and/or
 an amplitude less than the amplitude of the acoustic waves applied at step b).

According to one particular embodiment, at least a first and a second acoustic field generator are present along the length of the channel and:
 said first and second acoustic field generator emitting acoustic waves at steps b) and c), and
 said channel having first and second walls respectively situated opposite to said first and second acoustic field generators which have different thicknesses in such a manner that the acoustic waves applied at step c) have a node and/or an antinode which is located on said second wall.

This embodiment may advantageously allow the formed multilayer aggregate of objects to be located on one of the walls of the channel and thus to be easily isolated.

According to one particular embodiment, at least a first and a second acoustic field generator are present along the length of the channel for generating respectively the acoustic waves at steps b) and c), wherein:
 said first and second acoustic field generators emit acoustic waves at steps b) and c) which have substantially the same main frequency, and
 the width and/or thickness of the channel varies, optionally decreases, over at least a portion of its length in such a manner that the acoustic waves applied at step c) have a different number of, optionally less, acoustic nodes than the acoustic waves applied at step b).

According to one particular embodiment, the main frequency of the acoustic waves applied at step c) may be different from the main frequency of the acoustic waves applied at step b) in such a manner that the acoustic waves applied at step c) have a different number of, optionally less, acoustic nodes than the acoustic waves applied at step b).

According to one particular embodiment, the invention concerns a method comprising:
 a) providing objects at first, second and third superposed regions of the channel,
 b) obtaining first, second and third aggregates of objects, optionally by applying transverse acoustic waves, in particular stationary waves, within each region to objects, and
 c) putting said first, second and third aggregates in contact in order to form said multilayer aggregate of objects by submitting said first, second and third aggregates to:
  gravity in absence of acoustic waves, or to
  acoustic waves inducing forces displacing said first, second and third aggregates toward each other.

In a particular embodiment of the invention, at least one of the first and second, and optionally third, aggregates comprises at least 100, in particular at least 250, in particular at least 500, in particular at least 750, in particular at least 1000, in particular at least 1500, objects.

In a preferred embodiment of the invention, at least one of the first and second, and optionally third, aggregates comprises at least 100, in particular at least 250, in particular at least 500, in particular at least 750, in particular at least 1000, in particular at least 1500, cells.

In a preferred embodiment of the invention, each of the first and second, and optionally third, aggregates comprises at least 100, in particular at least 250, in particular at least 500, in particular at least 750, in particular at least 1000, in particular at least 1500, objects.

In a preferred embodiment of the invention, each of the first and second, and optionally third, aggregates comprises at least 100, in particular at least 250, in particular at least 500, in particular at least 750, in particular at least 1000, in particular at least 1500, cells.

As mentioned above, the present invention advantageously allows the quick and easy obtaining of cell aggregates, a 3D construct of hundreds of cells being preferably formed in a few seconds.

According to one particular embodiment, all or part of the method is carried out in a gravitational field of strength lower than or equal to 10 m/s$^2$, in particular 9.5 m/s$^2$, in particular 9 m/s$^2$, in particular 8.5 m/s$^2$, in particular 8 m/s$^2$, in particular 7.5 m/s$^2$, in particular 7 m/s$^2$, in particular 6.5 m/s$^2$, in particular 6 m/s$^2$, in particular 5.5 m/s$^2$, in particular 5 m/s$^2$, in particular 4.5 m/s$^2$, in particular 4 m/s$^2$, in particular 3.5 m/s$^2$, in particular 3 m/s$^2$, in particular 2.5 m/s$^2$, in particular 2 m/s$^2$, in particular 1.5 m/s$^2$, in particular 1 m/s$^2$, in particular 0.5 m/s$^2$.

In a particular embodiment, all or part of the method according to the invention is carried out in a gravitational field of strength substantially different from the strength of the gravitational field at the Earth's surface which is equal to 9.81 m/s².

By "a gravitational field of strength substantially different from the strength of the gravitational field at the Earth's surface", it is meant a gravitational field of strength that differs of at least 5% from 9.81 m/s².

It is particularly advantageous to use acoustic waves at step b) since in this case the method may not be significantly affected by the gravity conditions e.g. by the fact that the method is carried out in weightlessness or in Earth gravity conditions. Indeed, acoustic radiation force is generated by the interaction between an acoustic field and the matter, and this independently of gravitational field. Therefore, directing species to equilibrium positions, e.g. towards nodes e.g. in a standing wave field is analogue to have artificial gravity.

When acoustic waves are used at step b), the only difference is that the equilibrium position of the aggregates at 1 g is situated slightly underneath the equilibrium position at 0 g.

For example, at 0 g the equilibrium position of a cell aggregate may be placed at a pressure node and at 1 g it may be placed slightly underneath the node far away from the walls of the channel.

The method according to the invention is particularly advantageous when used in a gravitational field of strength lower than the strength of the gravitational field at the Earth's surface (g=9.81 m/s²). Indeed, when acoustic waves are used, e.g. ultrasonic standing waves, the acoustic force generated can gather the objects, e.g. wandering cells, without the need of any other external force.

The method according to the invention thus advantageously allows the obtaining of compact 3D constructs of objects, e.g. cells, even when carried out in a gravitational field of low strength, e.g. in weightlessness.

In a particular embodiment, the invention concerns a method as defined above wherein:
the liquid (L) is a cell culture medium, and
at least one of the first (110) and second (111), and optionally third, aggregates comprises cells, and
said cells are cultured while present in the at least one of said first (110), second (111), and optionally third, aggregates.

Thus, when carrying out the method according to the invention, cells present in at least one of the first and second, and optionally third, aggregates may be grown, the number of said cells being at least multiplied by 2 or even by 5 during the cell culture.

In a preferred embodiment, at least one tissue is formed by the cell culture, in particular a bone tissue being formed by the cell culture. The formed tissue is preferably a 3D tissue.

The cell culture is preferably carried out in a gravitational field of strength substantially different from, in particular lower than, the strength of the gravitational field at the Earth's surface.

Cell culture in microgravity shows a double interest.

First of all, in microgravity 3D tissues can be developed in buoyancy providing an ideal environment for adequate developed tissues, as in normal physiological conditions.

Second, it is advantageous, as mentioned above, to develop techniques of tissue engineering for astronaut needs, namely bone reconstruction and tissue damage replacement.

The present invention advantageously allows the gathering of wandering cells in microgravity without the need of any other external force, e.g. to make compact 3D constructs.

In a preferred embodiment, the first and second, and optionally third, aggregates are kept during at least one hour, in particular at least one day, in particular at least one week.

It is particularly preferred to apply acoustic waves to these first and second, and optionally third, aggregates to create an acoustic trap wherein stable aggregates can be kept consolidated during hours, days or weeks.

In a particular embodiment, some cell culture medium is introduced at least once in the channel during the cell culture.

In a particular embodiment, the cell culture medium is renewed at least once during the cell culture. The expression "the cell culture medium is renewed" means that the cell culture medium initially in contact with the aggregates is entirely replaced by another cell culture medium newly introduced in the channel, which can be of same or different chemical nature.

The invention advantageously allows the renewing of the cell culture medium without disturbing the aggregates since these aggregates are particularly stable. Such advantage is interesting because when not using the invention the culture medium may not be easily changed, indeed in microgravity conditions the flow may generate perturbations dragging out the aggregate.

In microgravity, shear stimulation of aggregates for improving tissue growth may be difficult because any perturbation generates uncontrolled displacement of the construct. While in the invention, vibrations or oscillations generating shear stresses can be applied while keeping the construct around a 3D equilibrium position.

In a particular embodiment, the first and second, and optionally third, aggregates are 3D aggregates.

In a particular embodiment, a plurality of sets of first and second, and optionally third, aggregates are present along a longitudinal axis of the channel.

In a preferred embodiment, a plurality of sets of first and second 3D aggregates are present along a longitudinal axis of the channel and said sets of aggregates were obtained by carrying out step b) in a gravitational field of strength lower than the strength of the gravitational field at the Earth's surface.

Acoustic Field Generator, Acoustic Waves and Levitation of Objects

The acoustic waves used at steps b) and/or c) may have a main frequency $f_{max}$ of 10 MHz or less, preferably comprised between 0.5 and 10 MHz.

The use of an acoustic field generator in such ranges of frequency may advantageously facilitate maintenance of the integrity of living cells or objects such as vesicles, liposomes, bacteria or viruses.

The acoustic waves used at steps b) and/or c) may advantageously be generated along a thickness of the channel.

The acoustic field generator may be a piezoelectric, e.g. ceramic.

It is for example possible to use an acoustic field generator sold under the reference PZ26 by the company Ferroperm Piezoceramics, Kvistgard, Denmark.

The part of the acoustic field generator in contact with a wall of the channel may be circular or rectangular.

The area of this part may be bigger or smaller than the channel area namely length by width. Said area may be equal to the channel area depending on the configuration needed for generating the aggregates.

The acoustic field generator may be powered by a sinusoidal tension. In a variant, the acoustic field generator may be powered by a triangular or square-wave tension.

The acoustic field generator may be digitally or analogically controlled.

The acoustic field generator may be powered by a wave generator for example the model 5062 sold by Tabor electronics, Israel.

The wave emitted by the wave generator may be amplified by an amplifier, such an amplifier is for example the model 9250 sold by Tabor electronics, Israel.

The wave generator may, during steps b) and/or c), generate waves having an amplitude comprised between 0 and 40 Vp-p (Volts peak to peak).

The acoustic energy density generated during steps b) and/or c) may be comprised between 1 and 1000 J/m³ (Joules/m³), for example between 1 and 300 J/m³, for example between 5 and 50 J/m³, and may for instance be of 10 J/m³.

The acoustic waves used at steps b) and/or c) may have a main frequency which is a resonant frequency of the channel along one of its transverse dimensions.

The transverse dimensions of the channel are the thickness and the width of the channel.

By "main frequency which is a resonant frequency of the channel along one of its transverse dimensions", it is meant a frequency $f_0$ such that a transverse dimension z of the channel, measured at a given position along the longitudinal axis of the channel, satisfies $$z = \frac{n\lambda}{2}$$

where n is an integer, and $$\lambda = \frac{c_f}{f_0}$$

where $c_f$ is the sound velocity in the liquid present in the channel at the temperature of said liquid, for example 20° C.

In other words, the frequency $f_0$ corresponds to the theoretical frequency satisfying, at a given position along the longitudinal axis of the channel, the resonance condition of the acoustic wave in the channel and the formation of a stationary wave along the considered transverse dimension.

The acoustic waves used at steps b) and/or c) may have a main frequency that is comprised between $0.5f_0$ and $1.5f_0$, in particular between $0.75f_0$ and $0.95f_0$ or between $1.05f_0$ and $1.25f_0$.

The use of such frequencies may advantageously allow the creation of an acoustic force which is strong enough to obtain desirable focusing of the objects.

The acoustic field generator may be fastened to one of the walls of the channel. This fastening may be done using any means known to the skilled artisan as appropriate, in particular by gluing.

A layer of an acoustic adaptation material may be present between the acoustic field generator and at least one of the walls of the channel.

The acoustic adaptation may be made by the use of any appropriate material known to the skilled artisan.

A plurality of acoustic field generators may be present along the length of the channel for generating said acoustic waves at steps b) and/or c), the acoustic field generators preferably being present on the same side of the channel.

Channel

According to the present invention, it is possible to use channels that are described in US 2008/0067128, the content of which is hereby incorporated by reference.

Geometric Features

The width and/or thickness of the channel may vary, optionally decrease, on at least a portion of its length.

Thus, when moving along the longitudinal axis of the channel, the thickness of said channel may be constant or may vary. The channel may in particular comprise at least two zones that axially follow one another and that present different thicknesses.

The channel may present, on at least a portion of its length, in particular on the totality of its length, a thickness that is less than or equal to 3 cm, better less than or equal to 1 cm. The channel is, for example, a micro-channel.

By "micro-channel", it is meant a channel having, over the totality of its length, a thickness that is less than or equal to 1 mm.

The channel may present on at least a portion of its length, in particular over the totality of its length, a thickness comprised between 50 µm and 3 mm, preferably between 100 µm et 500 µm.

The width of the channel may, when moving along the longitudinal axis of said channel, be constant or vary. The channel for example presents two zones that axially follow one another and that present different widths.

By "longitudinal axis of the channel", it is meant the line interconnecting the centers of gravity of the cross-sections of the channel. The longitudinal axis of the channel may be straight or curvilinear and may be contained in a plane which can be a plane of symmetry for some or even all of the cross-sections of the channel.

In an embodiment, the channel width may vary and the channel may be of a pyramidal shape when observed from above. In this particular case, the acoustic field generators may be rectangular or not.

In a variant, the channel may, when observed from above, have the shape of circles connected by sub-channels, in particular rectilinear sub-channels.

In the latter configuration, the acoustic field generators may be cylindrical, said configuration in particular enabling the generation of a mosaic of aggregates.

The channel may have over at least a portion of its length, in particular over the totality of its length, a width comprised between 1 mm and 40 mm, preferably between 5 mm and 20 mm.

The length of the channel, measured along its longitudinal axis, is, for example, comprised between 3 mm and 1000 mm, preferably between 10 mm and 500 mm.

The channel for example has a length of 100 mm, a width of 10 mm and a thickness of 0.4 mm.

According to another exemplary embodiment, the length of the channel may be comprised between 10 mm and 1000 mm, the width of the channel may be comprised between 1 mm and 40 mm and the thickness of the channel may be comprised between 0.5 mm and 3 mm.

The channel may comprise a transversal section that is substantially constant when displacing along its longitudinal axis.

The channel may have over at least a portion of its length, in particular over the totality of its length, a rectangular transversal section.

In a variant, the channel may have over at least a portion of its length, in particular over the totality of its length, a square or circular transversal section.

The channel may advantageously have ratios of width/thickness and/or length/thickness that are greater than or equal to 10.

Such ratios may advantageously prevent three-dimensional effects in the flow profile.

In a preferred embodiment, the channel has, over at least a portion of its length, in particular over the totality of its length, a rectangular transversal section and a ratio width/thickness ≥10.

Walls of the channel may be platelet-shaped.

Walls of the channel may have over at least part, in particular the totality, of their length a thickness comprised between 0.5 mm and 5 mm.

The channel may comprise, over at least a portion of its length, a wall whose thickness varies.

Such a configuration may allow the creation of an acoustic node or anti-node near the portion of the wall of different thickness and thereby cause the aggregates to contact one another near this region.

The wall opposite to the wall wherein the acoustic waves are generated may freely oscillate when the method according to the invention is carried out.

Inlet(s) and Outlet(s)

The channel may be in fluidic communication with at least one, in particular at least two, inlets.

The channel may be in fluidic communication with at least one, in particular at least two, outlets.

The channel comprising a plurality of inlets and/or of outlets, for instance two inlets and two outlets, may be placed in a stable frame or in a frame that may be tilted so as to modify the gravitational acceleration.

The channel inlet(s) and/or outlet(s) may be connected to syringe pumps and/or peristaltic pumps. When they are connected to peristaltic pumps, a hydrodynamic dampener may be added between the peristaltic pump and the channel inlet(s) and/or outlet(s).

The channel may be in fluidic communication with one or more outlet(s) where multilayer aggregates, formed by the method according to the invention, may be evacuated.

As such, it may not be necessary to open the channel in order to collect the formed multilayer aggregates.

Preferably, at least one of the inlet(s) presents a width that is not less than the width of the channel and/or presents a section that is substantially rectangular.

In an embodiment of the invention, at least one inlet opens out in one of the bottom and top walls of the channel and another inlet opens out in the other one of the bottom and top walls of the channel.

By way of example, two inlets are disposed facing each other.

In a variant, all the inlets open out either into the bottom wall or into the top wall of the channel.

In an embodiment of the invention, at least two inlets are offset relative to each other along the longitudinal axis of the channel.

At least one inlet may open out into the channel substantially parallel to or perpendicular to the longitudinal axis thereof.

In an embodiment of the invention, at least one feed orifice is in fluidic communication with at least one the inlet(s) via a duct, the duct including in particular a diverging portion that diverges from a tip of the duct, the feed orifice opening out into the duct adjacent to said tip, and in particular perpendicularly to the duct.

This diverging portion of the duct makes it possible to form a sheet of substance starting from a feed point.

In an embodiment of the invention, at least first and second outlets are in fluidic communication with the channel, and separated from each other by a transverse separation wall of non-zero height measured along the thickness of the channel.

The outlet(s) may allow recovery of the multilayer aggregate formed by the method according to the invention.

At least two outlets may be offset relative to each other along the longitudinal axis of the channel. In a variant, at least two outlets may be facing each other.

In an embodiment of the invention, the channel is in fluidic communication with at least first, second and third outlets, the second outlet being disposed between the first and third outlets along the thickness of the channel.

In an embodiment of the invention, at least one outlet orifice is in fluidic communication with the outlet(s) of the channel via a duct, the duct includes a portion of section that narrows laterally, in particular a portion converging towards a tip, said portion being triangular in shape when observed from above, for example, the outlet orifice opening out into the duct, e.g. adjacent to the tip, and in particular perpendicularly to the duct.

This converging portion of the duct may serve to avoid formation of a stagnation point at the outlet orifice.

Materials Constituting the Channel

The walls of the channel may comprise, in particular consist of, a material chosen among: organic or mineral glasses, quartz, thermoplastic materials, in particular PMMA or polycarbonate, and metals. More generally, it is possible to use any material having a high acoustic impedance, i.e. at least ten times greater than the acoustic impedance of the fluid.

The channel may be fabricated using conventional fabrication methods of the kind used in the field of micro fluidics.

Where appropriate, the microchannel may be provided with at least one valve, e.g. a solenoid valve.

Liquid and Objects

The liquid may be a biological liquid such as blood.

In a variant, the liquid may be water.

The liquid may be transparent to visible light.

The liquid may not be flowing during step b).

According to an embodiment, the liquid is flowing at least during steps b) and/or c), the Reynolds number of the flow of the liquid optionally being less than 10.

The objects may be monodisperse or polydisperse biological cells, in particular blood cells, for example globules.

In a particular embodiment, the objects have a positive acoustic contrast factor.

The "acoustic contrast factor" is defined as detailed below.

The acoustic radiation force has the expression:

$$F_{ac} = <E_{ac}> V_p k A(\rho,\beta) \sin(2ky),$$

with $<E_{ac}>$ the average acoustic energy density; $V_p$ the volume of the particle species, $k = 2\pi/\lambda$ with $\lambda$ the wave length of the ultrasonic wave and the acoustic contrast factor has the expression:

$$A(\rho,\beta) = [(5\rho_p - 2\rho_f)/(2\rho_p + \rho_f)] - \beta_p/\beta_f$$

wherein:

$\rho_p$ and $\rho_f$ are respectively particle p and suspending fluid f densities, $\beta_p$ and $\beta_f$ are respectively particle p and suspending fluid f compressibilities, and y is the distance from the standing wave nodal plane.

In a particular embodiment, the objects have a negative acoustic contrast factor.

In a particular embodiment, the objects are chosen among: bubbles, microbubbles, nanobubbles, droplets, fat cells, blood lipids, phospholipid vesicles, or mixtures thereof.

The objects having a negative acoustic contrast factor may be located after step b) at different pressure antinodes. In a variant, the objects having a negative acoustic contrast factor may be located between pressure nodes and pressure antinodes.

For example, first objects are located after step b) at a first pressure antinode and second objects are located after step b) at a second pressure antinode, said second pressure antinode being different from and superposed with the first pressure antinode, said second objects being different from said first objects, e.g. having different density or a different elastic constant. Said first and second objects may have a same size.

In a particular embodiment, the method comprises after step b) a determination of at least one feature of the objects, for example of at least one acoustic feature, e.g. of the acoustic impedance(s) of said objects.

In a particular embodiment, the method comprises after step b) a step of coalescence of the objects, said coalescence being in particular carried out in all or part when said objects are present in the channel.

In a particular embodiment, the objects are evacuated outside the channel, e.g. in a receptacle, after step c).

The objects may be rigid or deformable particles, for example polystyrene particles.

More generally, the objects may be rigid or deformable particles, polydisperse particles, biological cells, in particular blood cells, e.g. cancer cells in a blood or globule sample, bacteria, colloidal or non-colloidal emulsions, proteins or liposomes.

The average size of objects present in the channel may be less than or equal to 100 μm.

By "average size", it is meant the statistical granulometric dimension at the half of the population, known as D50.

The flow rates used may depend on the samples treated, the channel volume and the acoustic forces applied.

For instance, the liquid may be flowing during all or part of the method according to the invention at a flow rate comprised between 0.1 ml/min to 100 ml/min.

In a particular embodiment, the liquid may be flowing at a flow rate of 0.1 ml/min for a channel of volume 1 ml, when the maximum acoustic primary force is of the same order of magnitude as the gravity force, namely 1 pN (pico-Newton=$10^{-9}$) for latex particles or cells of 10 μm diameter.

The volume fraction of objects, measured when said objects are injected in the channel, may be 0.1% (v/v) or more. The volume fraction of objects corresponds to the [(volume of objects)/(volume of liquid containing said objects)]×100%

BRIEF DESCRIPTION OF THE DRAWINGS

The invention will be better understood from a reading of the detailed description below, of non-limiting examples for its implementation, and from examination of the attached drawings, in which:

FIG. 1 shows a device for carrying out of a method according to the invention, FIG. 2 shows an aggregate obtained according to a method of the invention, FIG. 3 is a view according to III-III of the channel used in FIG. 1.

DETAILED DESCRIPTION

Figure 4:
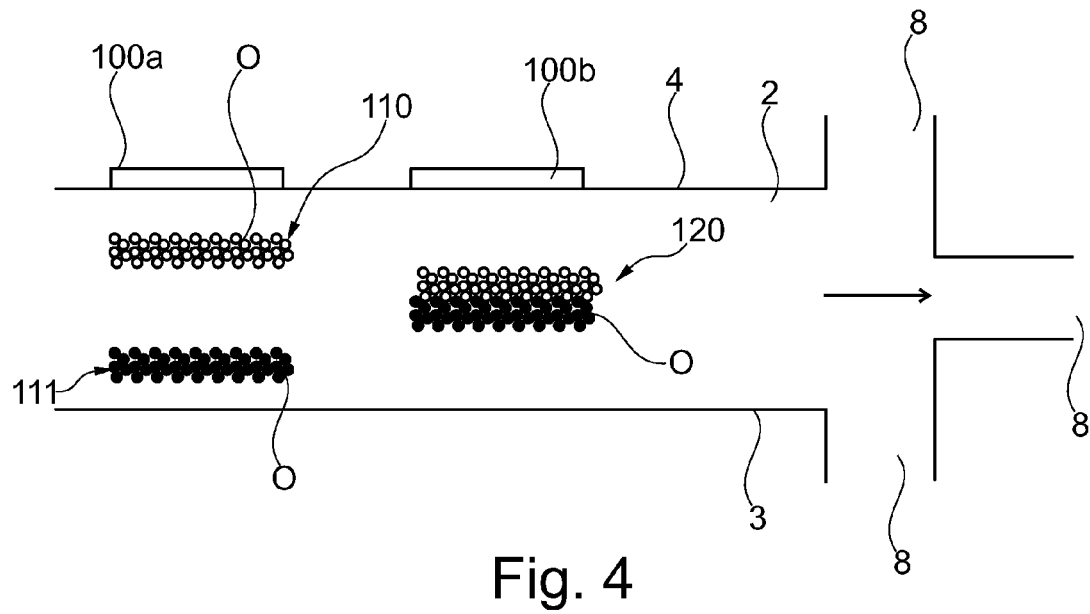
FIG. 4 is an example of evacuation of the multilayer aggregate formed according to the method shown in FIG. 1, FIGS. 5 to 8 are variants of devices for performing methods according to the invention.

FIG. 1 shows a device 1 which may be used in the methods according to the invention. The device 1 comprises a channel 2 extending along a longitudinal axis X.

The channel 2 may, as mentioned above, be a microchannel.

The channel 2 presents a cross-section that is for example rectangular. In the example described, the length/thickness ratio of the channel 2 is greater than 10.

The channel 2 has bottom and top walls 3 and 4. The channel 2 is as shown in fluidic communication with inlets 7, for example five inlets 7.

The inlets 7 open out in the top and bottom walls 4 and 3 of the channel 2 and four inlets 7 open out perpendicularly to the X axis as shown. Further, the inlet 7 that opens out in the top wall 4 of the channel 2 opens out into said channel 2 parallel to the X axis.

In a variant not shown, the inlets all open out into the bottom wall of the channel.

The inlets 7 are of substantially rectangular section, and of width equal to the width of the channel 2.

Inlets 7 are separated by transverse separation walls 10 that are perpendicular to the longitudinal axis X.

The inlets 7 present as shown thicknesses that are smaller than that of the channel 2, e.g. less than half its thickness.

In the embodiment shown in FIG. 1, some of the inlets 7 may be offset along the X axis such as separation walls 10.

At least one inlet 7 opens out, as shown, into a first zone 45 connected to a second zone 46 of greater thickness into which another inlet 7 opens out, the thicknesses being measured along the thickness of the channel 2.

The second zone 46 is connected to a central zone 47 of the channel 2.

The differences in thickness between the zones 45 and 46, and between the zones 46 and 47, correspond to the difference in height between the separation walls 10.

The device 1 can be used as follows in the methods according to the invention.

As shown in FIG. 1 for example, a carrier liquid L and a plurality of objects O are caused to flow via the inlets 7.

Objects O may be mono or polydisperse, said objects O may be biological cells and liquid L may be a biological liquid such as, e.g. blood.

Where appropriate, the device 1 may have one or more valves for controlling the injection of objects O via the inlets 7, where such a valve may, for example, be a solenoid valve presenting a single passage or multiple passages.

The injection of objects O via the inlets 7 can be controlled in frequency and in flow rate so as to enable the device 1 to operate continuously in order to process large volumes of objects.

Such a device 1 provides objects O at first 50 and second 60 superposed regions of the channel 2 (step a)) by a hydrodynamic focusing technique.

First 51 and second 61 layers of objects O are respectively present in said first 50 and second 60 superposed regions, the thickness of said first 51 and second 61 layers being controlled by hydrodynamic focusing.

The first 51 and second 61 layers of objects O are, as shown in FIG. 1, separated by a layer of pure liquid L. The objects O present in the first layer 51 may be identical to the objects O present in the second layer 61. In a variant, the objects O present in the first layer 51 and the objects O present in the second layer 61 belong to different species. In a variant, the objects O present in the first layer 51 have a different size from objects O present in the second layer 61.

Such layers of objects may undergo hydrodynamic shear induced diffusion [3] that can be detrimental for multi-levitation under-flow.

Thus, the device 1 is provided with acoustic field generators 100a and 100b which are, as shown, fastened to the top wall 4 of the channel 2. In FIG. 1, the acoustic field generators 100a and 100b are arranged along the channel 2 and present on the same side of said channel 2. In a variant not shown, the acoustic field generators may be arranged along the channel and present on opposite sides of said channel.

The acoustic field generator 100a enables formation, at step b), of first 110 and second 111 aggregates of objects O. As shown in FIG. 1, the objects O are placed in multi-levitation around the pressure nodes of the waves generated by the acoustic field generator 100a. In other words, each of the first 110 and second 111 aggregates is positioned at a different pressure node at the end of step b). The acoustic field generator 100a may operate at a frequency allowing the formation of a standing wave comprising two nodes along the thickness of the channel 2. In a variant, the acoustic field generator 100a does not produce a standing wave along the thickness of the channel 2, but is able to create an acoustic force field that enables formation of aggregates.

The expression "acoustic levitation" is employed when acoustic manipulation seeks to place objects in an equilibrium position against gravity. The equilibrium position depends on the acoustic properties of the objects and the suspending liquid, the acoustic power and the position and number of nodes of the acoustic waves. When particles or aggregates of the same or different species are in different equilibrium positions (levitating) in the channel, the expression "acoustic multi-levitation" is employed.

The liquid L may be flowing during the method according to the invention and the formation of the first 110 and second 111 aggregates at step b) may be done without a stop-flow period.

The acoustic focusing opposes the hydrodynamic shear induced diffusion mentioned above.

Step b) may have a duration comprised between 0.1 s to 5 minutes.

In other variants not shown, the methods according to the invention enable the formation of multilayer aggregates comprising three or more layers.

As explained above, an aggregate of objects may be more compact than a layer of objects. FIG. 2 shows an upper view of the first aggregate 110 obtained at the end of step b) according to the invention. The first aggregate 110 comprises a set of objects O that are in contact with each other, e.g. at least 50% of the objects O constituting said aggregate 110 can be in contact with each other.

The invention may enable the formation of 2D and/or 3D aggregates, e.g. depending on the strength of the acoustic field and the hydrodynamic parameters used. The definition of such 2D and 3D aggregates is given below.

Further, the first aggregate 110 comprises a succession 110$_1$ of objects O when moving along the Y axis which corresponds to a displacement along the width of the channel 2. The first aggregate 110 also comprises a succession of objects O when moving along the thickness of the channel 2. The first aggregate 110 is thus a 3D-aggregate.

In an embodiment, the aggregate comprises a succession of objects when moving along the width of the channel but has a thickness formed of at least one object. In this case, the aggregate is a 2D-aggregate.

Turning back to FIG. 1, an example of step c) according to the invention will now be detailed. In FIG. 1, the first 110 and second 111 aggregates are brought into contact to form a multilayer aggregate 120 of objects O. Said multilayer aggregate 120 is formed by submitting the first 110 and second 111 aggregates to acoustic waves inducing displacement of said first 110 and second 111 aggregates toward each other.

These acoustic waves are generated by an acoustic field generator 100b which may operate at a frequency allowing the formation of a standing wave comprising one node along the thickness of the channel 2. In a variant, the acoustic field generator 100b does not produce a standing wave along the thickness of the channel 2 but is able to create an acoustic force field that enables formation of the multilayer aggregate.

In the example shown in FIG. 1, step c) comprises submitting the aggregates 110 and 111 to acoustic waves having less acoustic nodes than the acoustic waves applied at step b). Further, in the example shown, the acoustic node formed at step c) has a transverse position which is different from the transverse positions of the acoustic nodes of the acoustic waves applied at step b).

The aggregates 110 and 111 may thus pass through an area where the number of nodes decreases, leading to the refocusing of the formed aggregates, thereby generating the multilayer aggregate 120.

Step c) may have a duration comprised between 10 seconds and 60 minutes.

As shown in FIG. 3, a layer of a gel 101 acting as an acoustic impedance adapter may be present between the acoustic field generator 100a and the top wall 4 of the channel 2.

FIG. 4 shows the evacuation of the multilayer aggregate 120 formed in the method illustrated in FIG. 1.

In the embodiment shown in FIG. 4, the channel 2 is in fluidic communication with a plurality of outlets 8. The channel 2 may, as shown, be connected to three outlets 8, two of these outlets 8 may face each other and one may open out, one into the bottom wall 3 of the channel 2, and the other into the top wall 4, as shown in FIG. 4.

The formed multilayer aggregate 120 may be discharged through the central outlet, this can be extended to a multi-layer aggregate of 3 layers or more.

Figure 5:
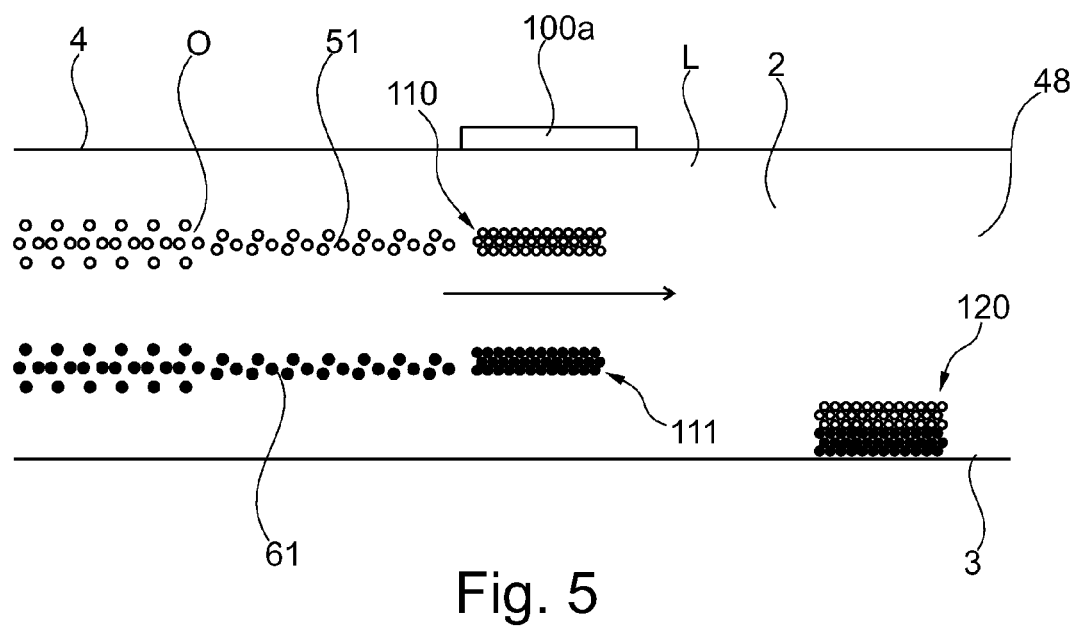

Another embodiment of a method according to the invention is illustrated in FIG. 5. In this figure, first 110 and second 111 aggregates are formed at the end of step b) e.g. in the same manner as in FIG. 1.

However, in this case, first 110 and second 111 aggregates are brought into contact to form the multilayer aggregate 120 by submitting said first 110 and second 111 aggregates to gravity in the absence of acoustic waves.

In this example, the first 110 and second 111 aggregates may enter a zone 48 wherein the intensity of the acoustic field is reduced, in particular where there is no acoustic field. Said aggregates 110 and 111 may thus be allowed to settle to form the multilayer aggregate 120.

In a variant, the first and second aggregates 110 and 111 at step b) may be formed after a stop-flow period and then the frequency and/or amplitude of the acoustic waves can be tuned in order to allow aggregates 110 and 111 settle for generating thickness and composition-controlled multilayer aggregate 120.

Figure 6:
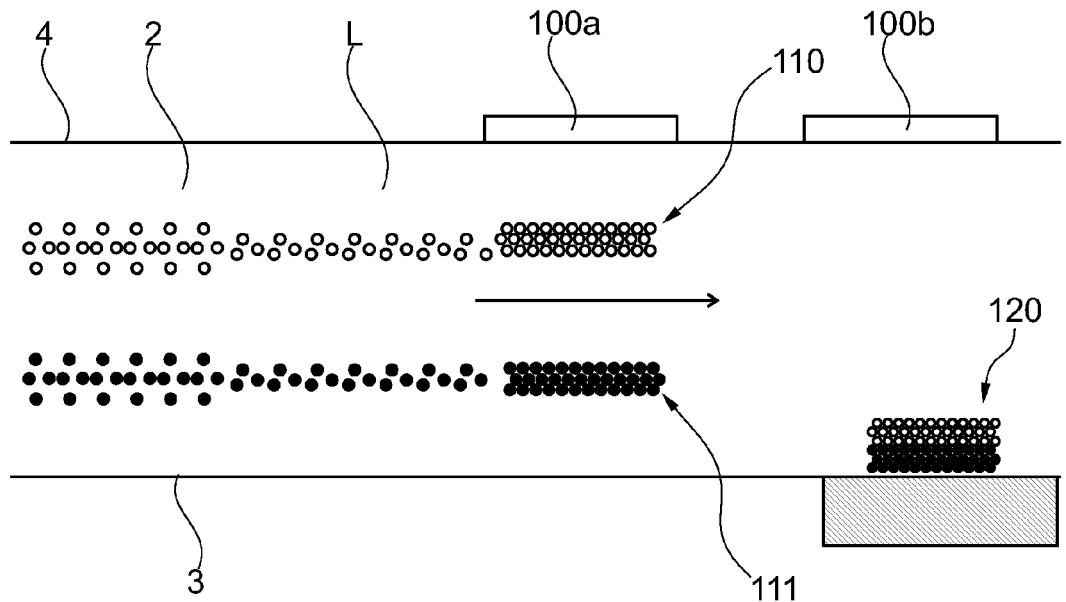

In the example shown in FIG. 6, first and second aggregates 110 and 111 are formed as detailed in the embodiment shown in FIG. 1. However, the bottom wall 3 of the channel 2 has a varying thickness. In this example, the variation in the thickness of the bottom wall 3 may allow the acoustic waves generated by the acoustic field generator 100b to have a node or an antinode which is located on the bottom wall 3. In this case, the first 110 and second 111 aggregates may be displaced, during step c), towards the bottom wall 3 of the channel 2 and, as shown, the second aggregate 111 may be put into contact with said bottom wall 3.

The formed multilayer aggregate 120 will be located on the bottom wall 3 of the channel 2.

Figure 7:
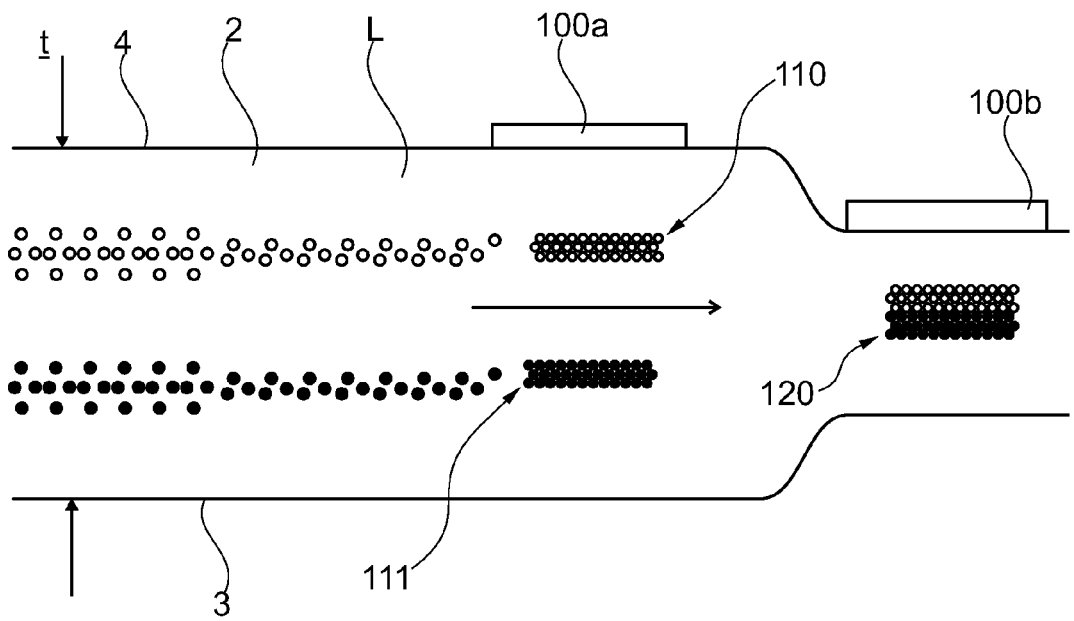

FIG. 7 shows another embodiment wherein the thickness t of the channel 2 decreases over at least a portion of its length in such a manner that the acoustic waves applied at step c) have fewer acoustic nodes than the acoustic waves applied at step b). In the example shown, the first 100a and second 100b acoustic field generators emit acoustic waves at steps b) and c) which have substantially the same main frequency.

In a variant not shown, the first and second acoustic field generators emit acoustic waves at steps b) and c) which have a main frequency that is different. The difference between the main frequencies may enable creation at step c) of acoustic waves having a different number of, optionally less, acoustic nodes than the acoustic waves applied at step b).

In a variant not-shown, the thickness of the channel increases over at least a portion of its length in such a manner that the acoustic waves applied at step c) have a different number of acoustic nodes than the acoustic waves applied at step b).

In a variant not-shown, the aggregates can be brought into contact to form said multilayer aggregate of objects by increasing the number of nodes/antinodes.

Figure 8:
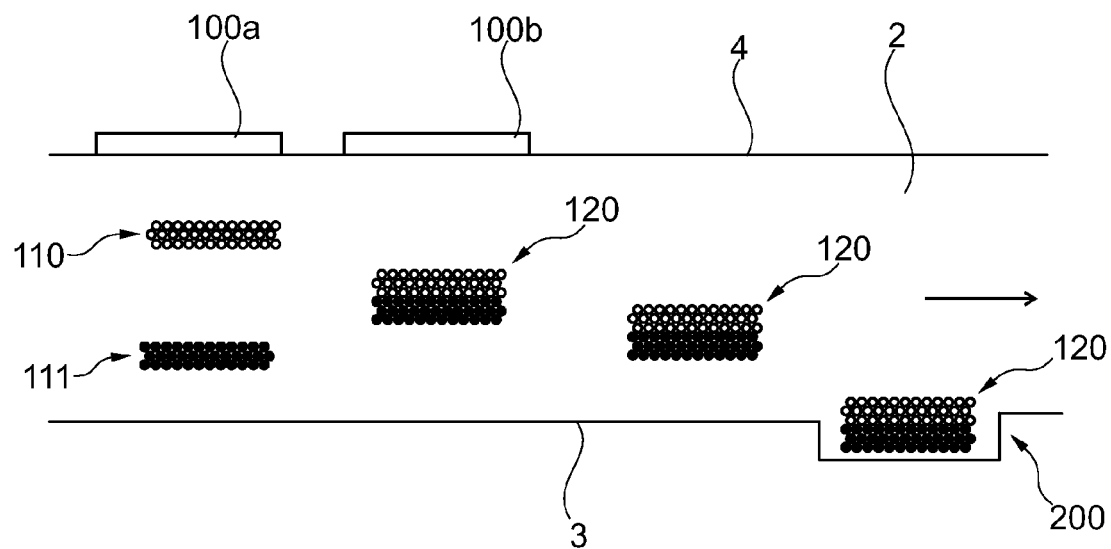

FIG. 8 shows a possible configuration to remove the multilayer aggregates 120 formed along the channel 2.

A series of multilayer aggregates 120 can be formed along the channel 2 and the flow can then be stopped. A series of wells 200 placed at the opposing wall 3 to the first 100a and second 100b acoustic field generators can be used for receiving the multilayer aggregates 120.

The formed multilayer aggregates 120 are then transported to the wells 200 using slow flow. This disposal system of multilayer aggregates 120 can be produced in series.

Figure 9:
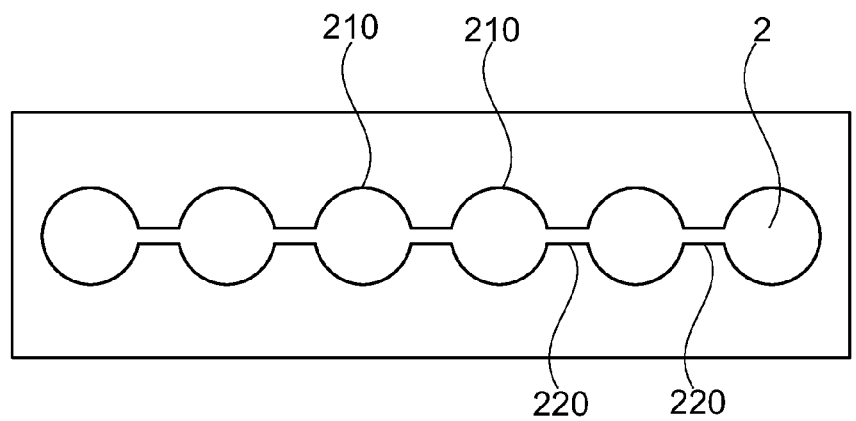
FIG. 9 is an embodiment of a channel that may be used in the methods according to the invention, and FIGS. 10 to 12 B show experimental results obtained by the methods according to the invention.

FIG. 9 shows an embodiment of channel 2 observed from above which has the shape of circles 210 connected by channels 220 as shown in FIG. 9. In the latter configuration, the acoustic field generators can be cylindrical and a mosaic of aggregates can be generated.

Examples

Experimental results obtained by the methods according to the invention are hereunder detailed.

Figure 10:
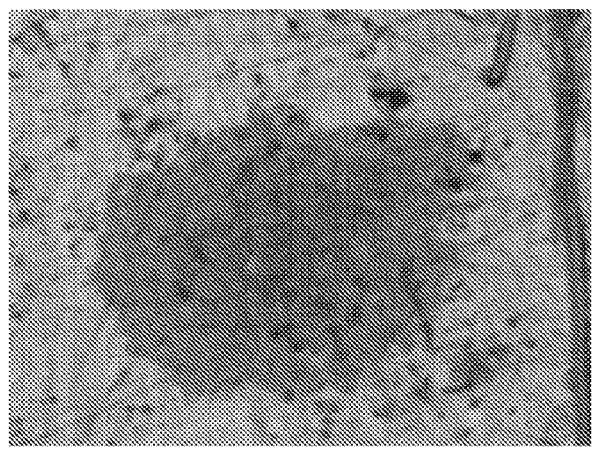

FIG. 10 shows a cancer cell 2D aggregate in levitation obtained in a channel of 250 μm thickness.

Figure 11A:
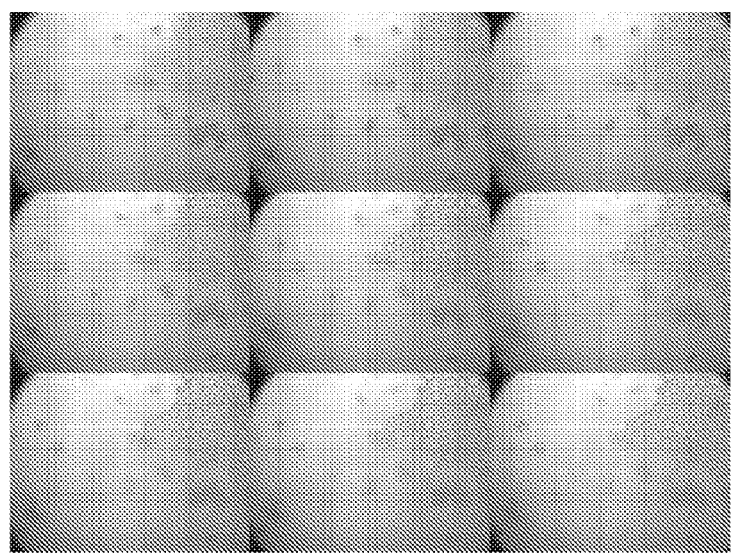
Figure 11B:
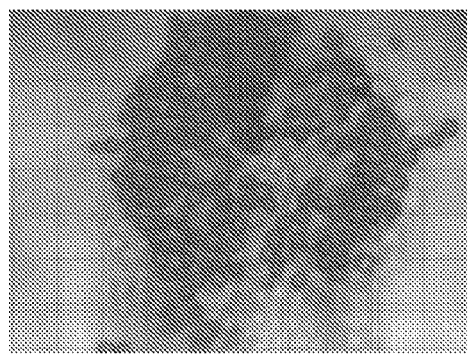

FIGS. 11 A and 11 B show the multilevitation of particles. Particles of two species: latex and silica particles both 10 μm diameter are in equilibrium at two different positions in the thickness (250 μm) of the channel. FIG. 11A shows these particles at the end of step b) according to the invention and FIG. 11B shows these particles at the end of step c) according to the invention.

Figure 12A:
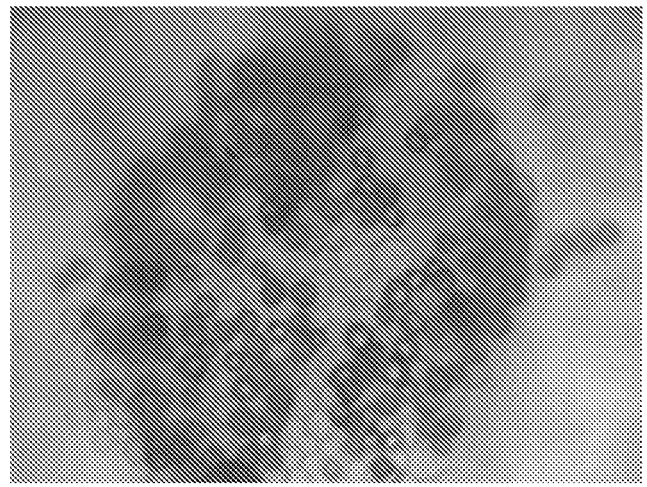

FIG. 12A shows two 2D layers of 10 μm latex (dark) and silica (bright) particles forming a levitating bi-layer.

Figure 12B:
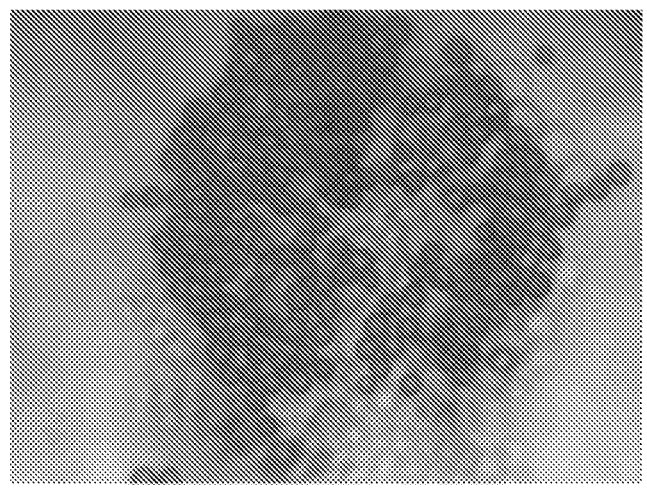

FIG. 12 B shows a bi-layer composed of a 3D latex particles aggregate and a silica particle aggregate.

REFERENCES

[1] Hoyos et al. Fluidic separation device: US2008/0067128 A1,
[2] Callens, et al. (2008) Analytical Chemistry 80, 4866-4875,
[3] Williams et al. (2008) Analytical Chemistry 80, 7105-7115,
[4] Kuznetsova et al. (2009) Biotechnology Progress 25(3), 834-841.

The expression "comprising a/one" should be understood as "comprising at least one".

The expression "of between" should be understood with the end points included.

The invention claimed is:

1. A method of forming a multilayer aggregate of objects in a channel comprising a liquid, said method comprising:
    a) providing objects at first and second superposed regions of the channel,
    b) obtaining first and second aggregates of objects within each region, and
    c) bringing said first and second aggregates into contact to form said multilayer aggregate of objects by submitting said first and second aggregates to:
       gravity in absence of acoustic waves, or to
       acoustic waves inducing displacement of said first and second aggregates toward each other.

2. The method according to claim 1, wherein:
    in step b), the first aggregate being obtained by applying transverse acoustic waves to the objects within the first region, the second aggregate being obtained by applying transverse acoustic waves to the objects within the second region and the acoustic waves used at step b) being generated along a thickness of the channel, or
    in step c) said first and second aggregates being brought into contact to form said multilayer aggregate of objects by submitting said first and second aggregates to acoustic waves and the acoustic waves used at step c) being generated along a thickness of the channel.

3. The method according to claim 1, in step b), the first aggregate being obtained by applying transverse acoustic waves to the objects within the first region, the second aggregate being obtained by applying transverse acoustic waves to the objects within the second region and in step c) said first and second aggregates being brought into contact to form said multilayer aggregate of objects by submitting said first and second aggregates to acoustic waves, step c) comprising submitting the aggregates to acoustic waves having at least one of:
    a different number of acoustic nodes than the acoustic waves applied at step b),
    at least one acoustic node having a transverse position which is different from the transverse position(s) of the acoustic node(s) of the acoustic waves applied at step b),
    at least one acoustic antinode having a transverse position which is different from the transverse position(s) of the acoustic antinode(s) of the acoustic waves applied at step b), and an amplitude less than the amplitude of the acoustic waves applied at step b).

4. The method according to claim 1, the channel comprising, over at least a portion of its length, a wall whose thickness varies.

5. The method according to the claim 4, in step c) said first and second aggregates being brought into contact to form said multilayer aggregate of objects by submitting said first and second aggregates to acoustic waves, at least a first and a second acoustic field generator being present along the length of the channel and:
said first and second acoustic field generator emitting acoustic waves at step b) for obtaining aggregates of first and second objects and emitting the acoustic waves at step c), and
said channel having first and second walls respectively situated opposite to said first and second acoustic field generators which have different thicknesses in such a manner that the acoustic waves applied at step c) have a node or an antinode which is located on said second wall.

6. The method according to claim 1, the width or thickness of the channel varying over at least a portion of its length.

7. The method according to claim 6, in step c) said first and second aggregates being brought into contact to form said multilayer aggregate of objects by submitting said first and second aggregates to acoustic waves and, in step b), the first aggregate being obtained by applying transverse acoustic waves to the objects within the first region and the second aggregate being obtained by applying transverse acoustic waves to the objects within the second region, at least a first and a second acoustic field generator being present along the length of the channel for generating respectively the acoustic waves at steps b) and c), wherein:
said first and second acoustic field generators emit acoustic waves at steps b) and c) which have substantially a same main frequency, and
the width or thickness of the channel varies over at least a portion of its length in such a manner that the acoustic waves applied at step c) have a different number of acoustic nodes than the acoustic waves applied at step b).

8. The method according to claim 1, in step c) said first and second aggregates being brought into contact to form said multilayer aggregate of objects by submitting said first and second aggregates to acoustic waves and, in step b), the first aggregate being obtained by applying transverse acoustic waves to the objects within the first region and the second aggregate being obtained by applying transverse acoustic waves to the objects within the second region, a main frequency of the acoustic waves applied at step c) being different from a main frequency of the acoustic waves applied at step b) in such a manner that the acoustic waves applied at step c) have a different number of acoustic nodes than the acoustic waves applied at step b).

9. The method according to claim 1 comprising:
a) providing objects at first, second and third superposed regions of the channel,
b) obtaining first, second and third aggregates of objects within each region to objects, and
c) putting said first, second and third aggregates in contact in order to form said multilayer aggregate of objects by submitting said first, second and third aggregates to:
gravity in absence of acoustic waves, or to
acoustic waves inducing forces displacing said first, second and third aggregates toward each other.

10. The method according to claim 1, wherein layers of objects at the first and second superposed regions of the channel are provided at step a).

11. The method according to a claim 1, wherein the objects present in the first region, at step a), have a different size or nature from objects present, at step a), in the second region.

12. The method according to claim 1, objects being mono or polydisperse biological cells, stem cells or primary cell lines.

13. The method according to claim 1, said objects having a positive acoustic contrast factor.

14. The method according to claim 1, said objects having a negative acoustic contrast factor.

15. The method according to claim 14, said objects being selected from the group consisting of bubbles, microbubbles, nanobubbles, droplets, fat cells, blood lipids, phospholipid vesicles, and mixtures thereof.

16. The method according to claim 1, the method comprising after step b) a determination of at least one feature of the objects.

17. The method according to claim 1, the method comprising after step b) a step of coalescence of the objects.

18. The method according to claim 1, said objects being evacuated outside the channel after step c).

19. The method according to claim 1, at least one of the first and second aggregates comprising at least 100 objects.

20. The method according to claim 1, wherein:
in step b), the first aggregate being obtained by applying transverse acoustic waves to the objects within the first region and the second aggregate being obtained by applying transverse acoustic waves to the objects within the second region, a plurality of acoustic wave generators being present along the length of the channel for generating said acoustic waves at step b), or
in step c), said first and second aggregates being brought into contact to form said multilayer aggregate of objects by submitting said first and second aggregates to acoustic waves and a plurality of acoustic wave generators being present along the length of the channel for generating said acoustic waves at step c).

21. The method according to claim 1, the liquid being flowing at least during steps b) or c).

22. The method according to claim 1, the liquid not being flowing during step b).

23. The method according to claim 1, all or part of the method being carried out in a gravitational field of strength lower than or equal to 10 m/s$^2$.

24. The method according to claim 1, all or part of the method being carried out in a gravitational field of strength substantially different from the strength of the gravitational field at the Earth's surface.

25. The method according to claim 1, wherein:
the liquid is a cell culture medium, and
at least one of the first and second aggregates comprises cells, and
said cells being cultured while present in the at least one of said first and second aggregates.

26. The method according to claim 25, at least one tissue being formed by the cell culture.

27. The method according to claim 26, a bone tissue being formed by the cell culture.

28. The method according to claim 27, some cell culture medium being introduced at least once in the channel during the cell culture.

29. The method according to claim 27, the cell culture medium being renewed at least once during the cell culture.

30. The method according to claim 1, the first and second aggregates being kept during at least one hour.

31. The method according to claim 1, the first and second aggregates being 3D aggregates.

32. The method according to claim 1, a plurality of sets of first and second aggregates being present along a longitudinal axis of the channel.

* * * * *